(12) United States Patent
Madi et al.

(10) Patent No.: US 12,365,237 B2
(45) Date of Patent: Jul. 22, 2025

(54) FUEL CELL EXHAUST SYSTEM FOR FUEL CELL ELECTRIC VEHICLE

(71) Applicant: Nikola Corporation, Phoenix, AZ (US)

(72) Inventors: Abdulhadi Madi, Tempe, AZ (US); William Marley, Kansas City, MO (US); Narendra Purania, Troy, MI (US); Daniel Widhalm, Phoenix, AZ (US)

(73) Assignee: NIKOLA CORPORATION, Phoenix, AZ (US)

( * ) Notice: Subject to any disclaimer, the term of this patent is extended or adjusted under 35 U.S.C. 154(b) by 356 days.

(21) Appl. No.: 18/160,400

(22) Filed: Jan. 27, 2023

(65) Prior Publication Data

US 2023/0264565 A1 Aug. 24, 2023

Related U.S. Application Data

(60) Provisional application No. 63/311,654, filed on Feb. 18, 2022.

(51) Int. Cl.
*B60K 13/04* (2006.01)
*B60L 50/72* (2019.01)
*H01M 8/0444* (2016.01)

(52) U.S. Cl.
CPC ............ *B60K 13/04* (2013.01); *B60L 50/72* (2019.02); *H01M 8/04462* (2013.01); *H01M 2250/20* (2013.01)

(58) Field of Classification Search
None
See application file for complete search history.

(56) References Cited

U.S. PATENT DOCUMENTS

| 2008/0041034 | A1 | 2/2008 | Hosoi | |
|---|---|---|---|---|
| 2009/0075152 | A1* | 3/2009 | Horji | B62K 5/027 429/444 |
| 2013/0094842 | A1* | 4/2013 | Ohtsuka | H01M 8/04014 137/561 A |
| 2016/0056482 | A1* | 2/2016 | Otsuka | H01M 8/0444 180/220 |

(Continued)

FOREIGN PATENT DOCUMENTS

WO 2022028859 2/2022

OTHER PUBLICATIONS

International Searching Authority, International Search Report and Written Opinion, dated Jun. 27, 2023 with International Application No. PCT/US2023/011699.

*Primary Examiner* — Erez Gurari
(74) *Attorney, Agent, or Firm* — SNELL & WILMER L.L.P.

(57) ABSTRACT

An exhaust duct of a fuel cell exhaust system includes a convolute duct, a resonator coupled to and in fluid communication with the convolute duct, a mid-duct coupled to and in fluid communication with the resonator, and a tail duct coupled to and in fluid communication with the mid-duct, the tail duct comprising a lower duct and an upper duct. The upper duct includes an incline duct, a transition duct, a decline duct, and a hydrogen sensor having a portion positioned within the transition duct. A first portion of an exhaust is diverted to the lower duct and a second portion of the exhaust is diverted to the upper duct and measured by the hydrogen sensor to determine hydrogen content of the exhaust.

20 Claims, 8 Drawing Sheets

(56) References Cited

U.S. PATENT DOCUMENTS

| | | | |
|---|---|---|---|
| 2016/0276682 A1* | 9/2016 | Yamamoto | B60L 58/30 |
| 2017/0113532 A1* | 4/2017 | Hirota | B62K 11/10 |
| 2017/0263962 A1* | 9/2017 | Koo | H01M 8/0662 |
| 2017/0282749 A1* | 10/2017 | Yamamoto | H01M 8/04201 |
| 2022/0102741 A1* | 3/2022 | Grosch | H01M 8/2475 |
| 2023/0264565 A1* | 8/2023 | Madi | H01M 8/04201 |
| | | | 180/309 |
| 2023/0378494 A1* | 11/2023 | Hammer | H01M 8/04067 |
| 2023/0378501 A1* | 11/2023 | Hammer | H01M 8/04291 |
| 2024/0297373 A1* | 9/2024 | Bang | H01M 8/04776 |

\* cited by examiner

FUEL CELL EXHAUST SYSTEM FOR FUEL CELL ELECTRIC VEHICLE

CROSS-REFERENCE TO RELATED APPLICATIONS

This application claims priority to and the benefit of U.S. Provisional Application No. 63/311,654 filed Feb. 18, 2022 entitled "FUEL CELL EXHAUST SYSTEM FOR FUEL CELL ELECTRIC VEHICLE," the entirety of which is incorporated by reference, including but not limited to those portions that specifically appear hereinafter, but except for any subject matter disclaimers or disavowals, and except to the extent that the incorporated material is inconsistent with the express disclosure herein, in which case the language in this disclosure shall control.

TECHNICAL FIELD

The present disclosure relates to exhaust systems, and more particularly, to fuel cell exhaust systems for fuel cell vehicles.

BACKGROUND

Fuel cell electric vehicles (FCEVs) facilitate oxidation-reduction (redox) reactions between oxygen and hydrogen in a fuel cell system to generate electrical energy. More specifically, as hydrogen enters the fuel cell system, electrons are disassociated from hydrogen molecules and passed through an external circuit in order to perform work, while protons are passed through an internal membrane. At the cathode, the protons recombine with the electrons and oxygen in an exothermic reaction to form water and heat, which are exhausted to the external environment along with some amount of unreacted hydrogen and air. Given the flammability of hydrogen, the exhaust should be monitored to identify potentially hazardous levels of hydrogen. However, moisture in the exhaust can have a detrimental effect on the ability to accurately measure the hydrogen content. Accordingly, improved fuel cell exhaust systems for FCEVs remain desirable.

SUMMARY

A fuel cell exhaust system for a fuel cell electric vehicle (FCEV) may comprise a first exhaust duct comprising a first tail duct, the first tail duct comprising a first lower duct and a first upper duct positioned vertically above the lower duct, a second exhaust duct comprising a second tail duct, the second tail duct comprising a second lower duct and a second upper duct positioned vertically above the lower duct, a first hydrogen sensor having a portion positioned within the first upper duct, and a second hydrogen sensor having a portion positioned within the second upper duct. A first portion of a first exhaust is diverted to the first upper duct and measured by the first hydrogen sensor to determine hydrogen content of the first exhaust, and a first portion of a second exhaust is diverted to the second upper duct and measured by the second hydrogen sensor to determine hydrogen content of the second exhaust.

In various embodiments, the first exhaust duct may be coupled to and in fluid communication with a first exhaust outlet of a first fuel cell stack and the second exhaust duct may be coupled to and in fluid communication with a second exhaust outlet of a second fuel cell stack. The first exhaust duct may comprise a first convolute duct coupled to and in fluid communication with the first exhaust outlet of the first fuel cell stack. The second exhaust duct may comprise a second convolute duct coupled to and in fluid communication with the second exhaust outlet of the second fuel cell stack. The first exhaust duct may further comprise a first resonator coupled to and in fluid communication with the first convolute duct and a first mid-duct coupled to and in fluid communication with the first resonator. The second exhaust duct may further comprise a second resonator coupled to and in fluid communication with the second convolute duct and a second mid-duct coupled to and in fluid communication with the second resonator. The first resonator may be angled downward relative to at least a portion of the first convolute duct. The second resonator may be angled downward relative to at least a portion of the second convolute duct. The first hydrogen sensor may comprise a shim configured to discharge static electricity.

An exhaust duct of a fuel cell exhaust system may comprise a convolute duct, a resonator coupled to and in fluid communication with the convolute duct, a mid-duct coupled to and in fluid communication with the resonator, and a tail duct coupled to and in fluid communication with the mid-duct, the tail duct comprising a lower duct and an upper duct. The upper duct may comprise an incline duct, a transition duct, a decline duct, and a hydrogen sensor having a portion positioned within the transition duct. A first portion of an exhaust may be diverted to the lower duct and a second portion of the exhaust is diverted to the upper duct and measured by the hydrogen sensor to determine hydrogen content of the exhaust.

In various embodiments, the tail duct may further comprise an inlet duct in fluid communication with the upper duct and the lower duct and an outlet duct in fluid communication with the upper duct and the lower duct. The inlet duct may diverge into the upper duct and the lower duct at a first fork. The upper duct and the lower duct may converge into the outlet duct at a second fork. The mid-duct may comprise at least two segments separated by at least one bend. The exhaust duct may comprise a first angle between the lower duct and the incline duct, a second angle between the lower duct and the decline duct, a third angle between the incline duct and the transition duct, and a fourth angle between the transition duct and the decline duct. The exhaust duct may further comprise a trapezoidal cutout between the upper duct and the lower duct. The exhaust duct may further comprise a mounting bracket coupled to the mid-duct configured to couple the exhaust duct directly or indirectly to a chassis of a fuel cell electric vehicle (FCEV).

A fuel gas management system of a fuel cell electric vehicle (FCEV) may comprise an air intake system coupled to and in fluid communication with a fuel cell system, a hydrogen storage system coupled to and in fluid communication with the fuel cell system, and a fuel cell exhaust system coupled to and in fluid communication with the fuel cell system, the fuel cell exhaust system comprising a first exhaust duct comprising a first lower duct and a first upper duct positioned vertically above the first lower duct, and a first hydrogen sensor having a portion positioned within the first upper duct. A portion of an exhaust may be diverted to the first upper duct and measured by the first hydrogen sensor to determine hydrogen content of the exhaust.

In various embodiments, the fuel gas management system further comprises a second exhaust duct comprising a second lower duct and a second upper duct positioned vertically above the second lower duct. The first exhaust duct may be coupled to and in fluid communication with a first exhaust outlet of a first fuel cell stack of the fuel cell system, and the second exhaust duct may be coupled to and in fluid communication with a second exhaust outlet of a second fuel cell stack of the fuel cell system.

The contents of this section are intended as a simplified introduction to the disclosure and are not intended to limit the scope of any claim. The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The accompanying drawings are included to provide a further understanding of the present disclosure and are incorporated in, and constitute a part of, this specification, illustrate various embodiments, and together with the description, serve to explain exemplary principles of the disclosure.

DETAILED DESCRIPTION

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, electrical, and/or mechanical changes may be made without departing from the spirit and scope of the disclosure. Thus, the detailed description herein is presented for purposes of illustration only and not of limitation.

For example, the steps recited in any of the method or process descriptions may be executed in any suitable order and are not necessarily limited to the order presented. Furthermore, any reference to singular includes plural embodiments, and any reference to more than one component or step may include a singular embodiment or step. Also, any reference to attached, fixed, connected, or the like may include permanent, removable, temporary, partial, full, and/or any other possible attachment option. Additionally, any reference to without contact (or similar phrases) may also include reduced contact or minimal contact.

In the context of the present disclosure, methods, systems, and articles may find particular use in connection with medium- and heavy-duty FCEVs. However, various aspects of the disclosed embodiments may be adapted for performance in a variety of other systems, including hybrid vehicles, compressed natural gas (CNG) vehicles, hythane (mix of hydrogen and natural gas) vehicles, and/or the like. As such, numerous applications of the present disclosure may be realized.

Figure 1:
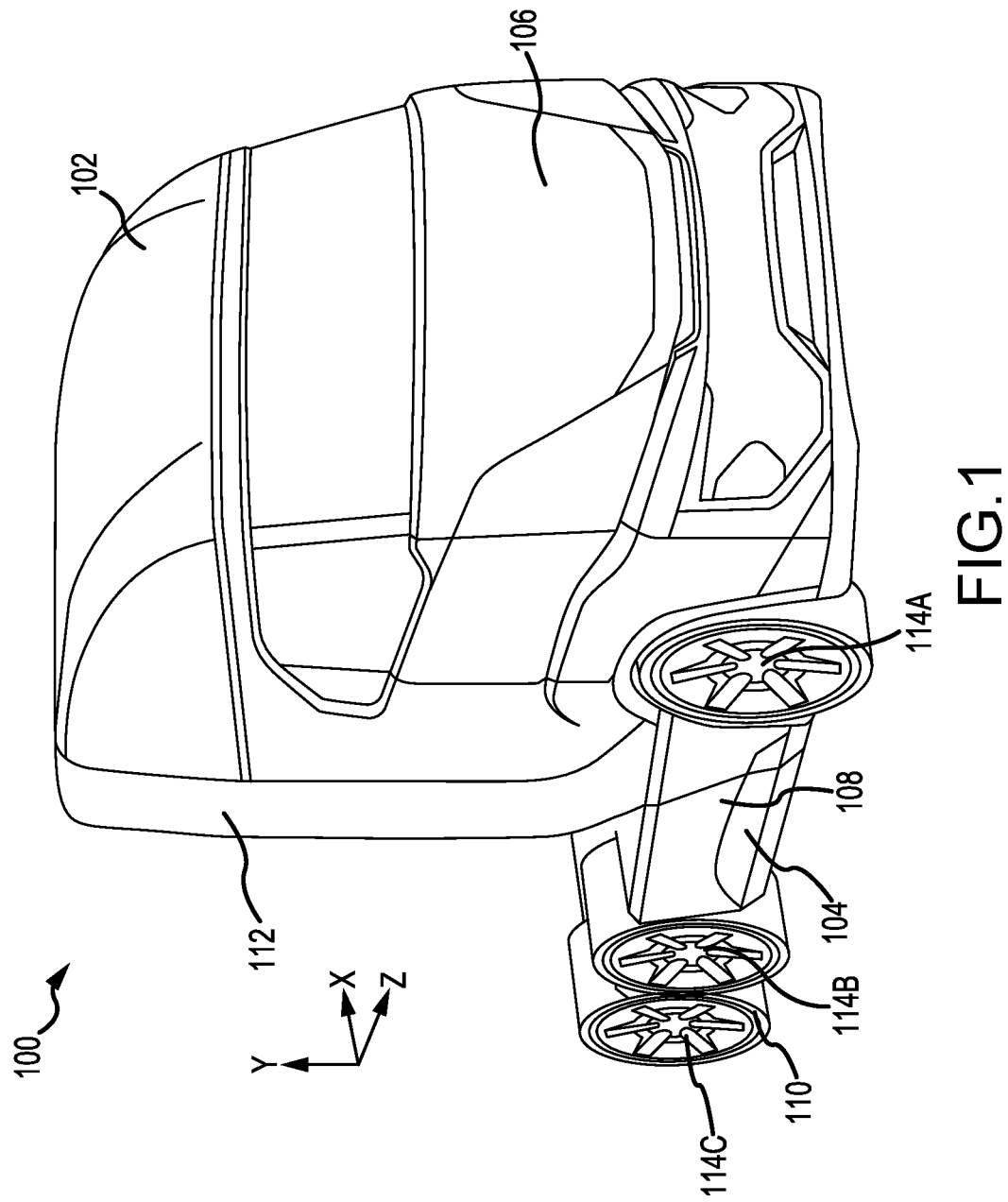
FIG. 1 illustrates a perspective view of an FCEV incorporating a fuel cell exhaust system, in accordance with various embodiments.

Accordingly, with reference to FIG. 1, an FCEV 100 is illustrated from a top perspective view, in accordance with various embodiments. As illustrated in FIG. 1, FCEV 100 is a heavy-duty FCEV. FCEV 100 is a tractor unit which may tow a trailer unit configured to hold and transport cargo. FCEV 100 may comprise a class 8, class 7, class 6, or any other weight classification of tractor-trailer combination. As described herein, FCEV 100 extends in a longitudinal direction along the Z-axis from a rear of FCEV 100 to a front of FCEV 100. FCEV 100 extends in a transverse direction along the X-axis from a passenger side of FCEV 100 to a driver side of FCEV 100. Finally, FCEV 100 extends in a vertical direction along the Y-axis from a ground surface on which FCEV 100 drives to a top of FCEV 100.

FCEV 100 comprises a cab 102 supported by a chassis 104. Cab 102 may be configured to shelter one or more vehicle operators or passengers from the external environment. In various embodiments, cab 102 comprises a door configured to allow ingress and egress into and from cab 102, one or more seats, a windshield, and numerous accessories configured to improve comfort for the operator and/or passenger(s). As illustrated in FIG. 1, FCEV 100 comprises a cab-over or cab-forward style tractor unit, but is not limited in this regard and may comprise any style of tractor unit including a conventional or American cab style tractor unit.

Chassis 104, otherwise known as the vehicle frame, is configured to support various components and systems of FCEV 100 including cab 102. Chassis 104 may comprise a ladder-like structure with various mounting points for FCEV 100's suspension, powertrain, energy storage systems (ESS) (for example, fuel cell system(s) and/or battery system(s)), and other systems. Chassis 104 supports and is coupled to a fuel cell system 106 which may be configured to facilitate an electrochemical reaction in order to generate electrical energy that can be used to drive FCEV 100 and operate electric components and systems of FCEV 100. Chassis 104 may be covered by one or more side covers 108 configured to provide corrosion-resistance and improved aerodynamics along the sides of FCEV 100. FCEV 100 further comprises wheels 110 comprising one or more tires coupled to one or more axles 114 and configured to roll along a driving surface. In various embodiments, FCEV 100 comprises a pair of single wheels coupled to a front axle 114A and a pair of dual wheels coupled to two rear axles (first rear axle 114B and second rear axle 114C). One or more of the axles may be driven. For example, in various embodiments, FCEV 100 may comprise a 6×2 configuration with a single driven axle; however, FCEV 100 is not limited in this regard and may comprise a 4×2, 6×4, 6×6, or other suitable configuration. In various embodiments, FCEV 100 may further comprise a hydrogen storage system 112 configured to contain and deliver hydrogen fuel to fuel cell system 106.

Figure 2:
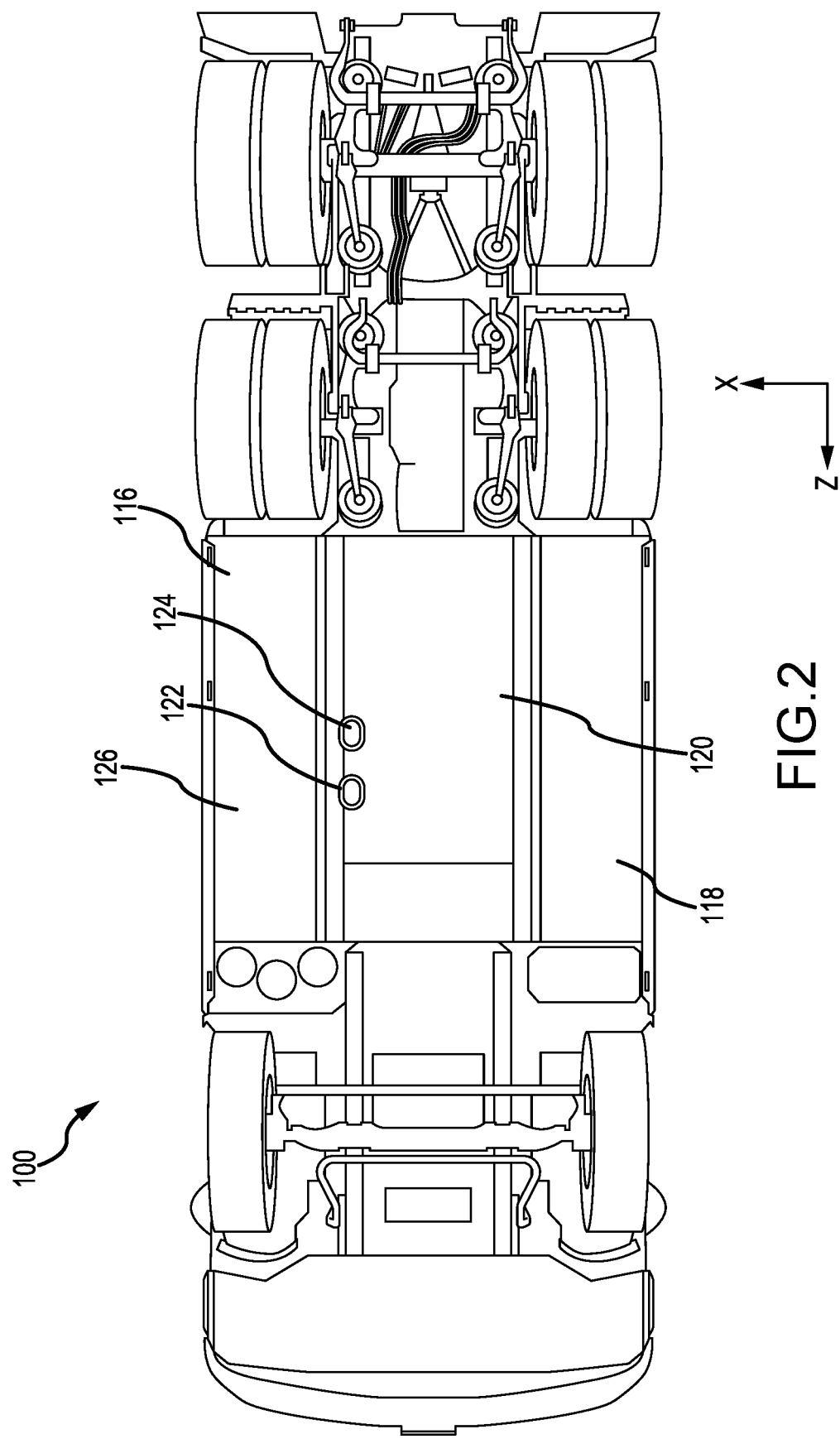
FIG. 2 illustrates a bottom view of an FCEV incorporating a fuel cell exhaust system, in accordance with various embodiments.

With reference to FIG. 2, FCEV 100 is illustrated from a bottom view, in accordance with various embodiments. In various embodiments, FCEV 100 comprises an undercarriage 116 that comprises a first outboard skid plate 118, an inboard skid plate 120, and a second outboard skid plate 126. First outboard skid plate 118 is positioned adjacent to the passenger side of FCEV 100 and is coupled to a first frame rail of chassis 104 on a first side and coupled to a first side cover 108 on a second side. Similarly, second outboard skid plate 126 is positioned adjacent to the driver side of FCEV 100 and is coupled to a second frame rail of chassis 104 on a first side and coupled to a second side cover 108 on a second side. Inboard skid plate 120 is positioned between the first outboard skid plate 118 and the second outboard skid plate 126 and is coupled to the first frame rail of chassis 104 on a first side and coupled to the second frame rail of chassis 104 on a second side.

Inboard skid plate 120 comprises a first exhaust aperture 122 and a second exhaust aperture 124 adjacent to and rearward of first exhaust aperture 122. As illustrated, first exhaust aperture 122 and second exhaust aperture 124 extend through inboard skid plate 120 adjacent to second outboard skid plate 126. More specifically, first exhaust aperture 122 and second exhaust aperture 124 are located adjacent to and inboard of the second frame rail of chassis 104 however, the positioning of first exhaust aperture 122 and second exhaust aperture 124 is not limited in this regard and the apertures may be positioned adjacent to and inboard of the first frame rail of chassis 104, centered in the transverse direction on inboard skid plate 120, or positioned at any suitable location in the transverse location on first outboard skid plate 118 or second outboard skid plate 126. Moreover, while illustrated as comprising two separate exhaust apertures, FCEV 100 is not limited in this regard and may comprise a single exhaust aperture in various embodiments.

In various embodiments, first exhaust aperture 122 and second exhaust aperture 124 are configured to permit exhaust gases and water to exit fuel cell system 106 (and FCEV 100) and be delivered to the external environment (for example, to the ground). More specifically, as fuel cell system 106 operates, fuel cell system 106 generates water and/or water vapor and heat to be exhausted to the external environment along with some amount of unreacted hydrogen and air. In various embodiments, first exhaust aperture 122 and second exhaust aperture 124 overlap with fuel cell system 106 in the transverse direction and are positioned rearward of fuel cell system 106. First exhaust aperture 122 and second exhaust aperture 124 may be located such that one or more exhaust ducts extending between fuel cell system 106 and the exhaust apertures occupy reduced and/or minimized volume on FCEV 100.

Figure 3:
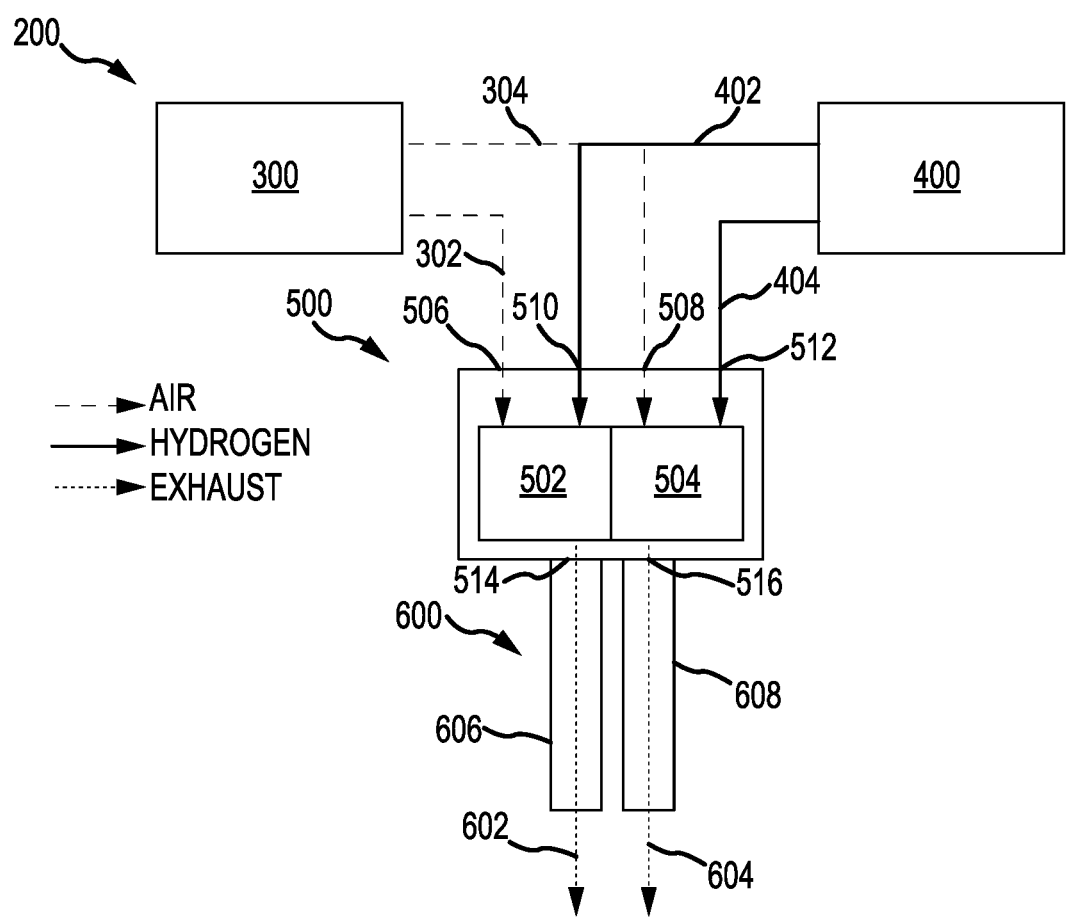
FIG. 3 illustrates a block diagram of a fuel gas management system of an FCEV, in accordance with various embodiment.

Referring now to FIG. 3, a block diagram of a fuel gas management system 200 of FCEV 100 is illustrated, in accordance with various embodiments. In various embodiments, fuel gas management system 200 may be incorporated into a heavy-duty FCEV, similar to FCEV 100 discussed in relation to FIGS. 1 and 2 above. Fuel gas management system 200 comprises an air intake system 300, a hydrogen storage system 400 (which may be the same as or similar to hydrogen storage system 112 discussed above), a fuel cell system 500 (which may be the same as or similar to fuel cell system 106 discussed above), and a fuel cell exhaust system 600.

Air intake system 300 may be configured to receive air from the external environment and deliver the air to fuel cell system 500. In various embodiments, oxygen required by fuel cell system 500 is delivered in the form of atmospheric air (which contains approximately 20-25% oxygen), via air intake system 300. Additionally or alternatively, oxygen required by fuel cell system 500 may be stored directly onboard FCEV 100 in one or more oxygen storage vessels configured to store and deliver oxygen gas to fuel cell system 500. In various embodiments, air intake system 300 comprises a first air intake and a second air intake. The first air intake and the second air intake may each comprise one or more components fluidly coupled together between an oxygen source (for example, the external environment or onboard oxygen stores) and fuel cell system 500. As such, the first air intake may define a first air intake pathway 302 and the second air intake may define a second air intake pathway 304. In various embodiments, air intake system 300 further comprises one or more compressors configured to compress incoming air or oxygen, thereby increasing the mass flow rate of air or oxygen traveling to fuel cell system 500. Moreover, in various embodiments, one or more components of the first air intake and the second air intake may be combined (such as the first and second intake snorkels and/or first and second filter assemblies) in order to reduce system complexity and/or part count.

Hydrogen storage system 400 may be configured to store and/or deliver hydrogen to fuel cell system 500. In various embodiments, hydrogen storage system 400 comprises a plurality of type III or type IV pressurized vessels positioned at the rear of cab 102 and/or on either side of chassis 104 between the frame rails of chassis 104 and side covers 108. In various embodiments, the pressurized vessels may be configured to contain pressurized gaseous or liquid hydrogen at a pressure of between approximately 6,000 and 14,000 pounds per square inch (psi), or between approximately 8,000 and 12,000 psi, or approximately 10,000 psi. As a result, the pressurized vessels of hydrogen storage system 400 may be configured to deliver hydrogen along a downward pressure gradient to fuel cell system 500 without the need for one or more compressors that may otherwise consume electrical energy and adversely impact vehicle range. Hydrogen storage system 400 may further comprise fluid routing components such as one or more filters, piping, valves, and control units configured to distribute and control the direction and quantity of flow of hydrogen to fuel cell system 500. Similar to air intake system 300, hydrogen storage system 400 may define one or more fluid pathways configured to deliver hydrogen to fuel cell system 500. In various embodiments, hydrogen storage system 400 defines a first hydrogen pathway 402 and a second hydrogen pathway 404 through which hydrogen may be delivered to fuel cell system 500.

In various embodiments, fuel cell system 500 comprises a proton-exchange membrane (PEM) fuel cell, phosphoric acid fuel cell, solid acid fuel cell, alkaline fuel cell, solid oxide fuel cell, molten-carbonate fuel cell, or other suitable fuel cell type. In various embodiments, fuel cell system 500 comprises a dual stack fuel cell system comprising a first fuel cell stack 502 and a second fuel cell stack 504. When coupled to FCEV 100, first fuel cell stack 502 is positioned closer to the front of FCEV 100 than second fuel cell stack 504 which may be adjacent to and rearward of first fuel cell stack 502. In various embodiments, fuel cell system 500 may be coupled to chassis 104 and positioned beneath cab 102; however, fuel cell system 500 is not limited in this regard and may be placed in any suitable position in FCEV 100.

First fuel cell stack 502 and second fuel cell stack 504 may each comprise multiple fuel cells, each comprising a membrane and a pair of catalyst layers (anode and cathode) sandwiched between a pair of gas diffusion layers. Each fuel cell may be capable of generating a small amount of electric potential (for example, approximately 0.7 volts), so multiple cells may be stacked (or placed in series) to increase voltage and power output. In various embodiments, first fuel cell stack 502 and second fuel cell stack 504 may each be capable of producing between approximately 0 and 200 kilowatts (kW), between approximately 50 and 150 kW, or approximately 100 kilowatts (kW) of power. As a result, the total power output produced by fuel cell system 500 may be between approximately 0 and 400 kW, between approximately 100 and 300 kW, or approximately 200 kW.

In various embodiments, first air intake pathway 302 is in fluid communication with first fuel cell stack 502. Second air intake pathway 304 is in fluid communication with second fuel cell stack 504. More specifically, first air intake pathway 302 is in fluid communication with a cathode of first fuel cell stack 502 through first air inlet 506 and second air intake pathway 304 is in fluid communication with a cathode of second fuel cell stack 504 through second air inlet 508, First hydrogen pathway 402 is in fluid communication with an anode of first fuel cell stack 502 through first hydrogen inlet 510. Second hydrogen pathway 404 in fluid communication with an anode of second fuel cell stack 504 through second hydrogen inlet 512.

As hydrogen enters the anodes of first fuel cell stack 502 and second fuel cell stack 504, respectively, catalysts in the anodes may disassociate electrons from protons in the hydrogen molecules. The positively charged protons are permitted to pass through the membrane while electrons are forced to travel through an external circuit (including high and/or low voltage electrical systems of FCEV 100) to perform work. The electrons recombine with the protons and oxygen at the cathodes of first fuel cell stack 502 and second fuel cell stack 504 to form water (or water vapor) and heat. This water and heat, along with some amount of unreacted hydrogen and air, may exit fuel cell system 500 via fuel cell exhaust system 600. More specifically, exhaust gases exit a first exhaust outlet 514 of first fuel cell stack 502 and a second exhaust outlet 516 of second fuel cell stack 504. From first exhaust outlet 514 and second exhaust outlet 516, the exhaust may exit FCEV 100 through a first exhaust pathway 602 and a second exhaust pathway 604, respectively, in various embodiments, first exhaust pathway 602 is defined by a first exhaust duct 606 that is coupled to and in fluid communication with first exhaust outlet 514 of first fuel cell stack 502. Likewise, second exhaust pathway 604 is defined by a second exhaust duct 608 that is coupled to and in fluid communication with second exhaust outlet 516 of second fuel cell stack 504.

Figure 4A:
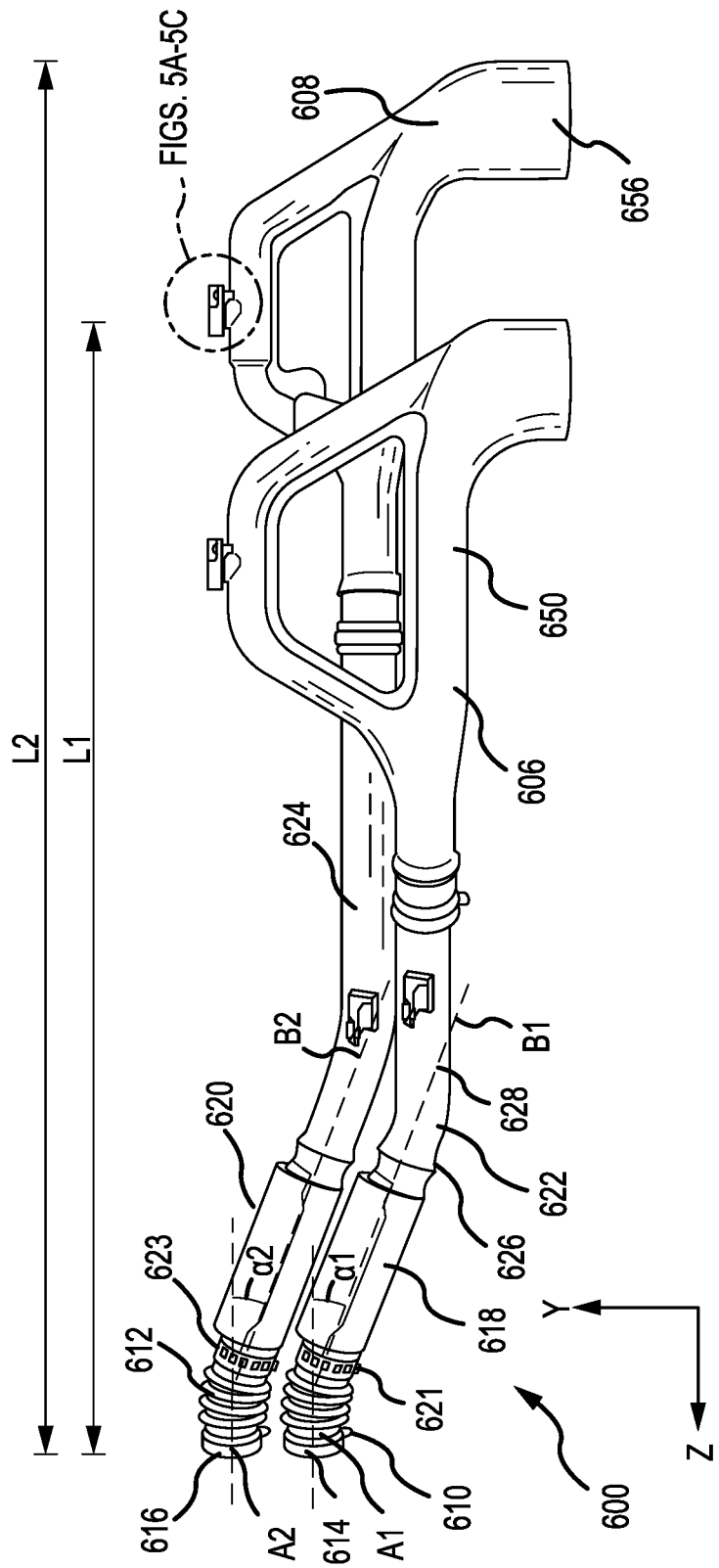
FIGS. 4A-4D illustrate various views of a fuel cell exhaust system, in accordance with various embodiments.
Figure 4B:
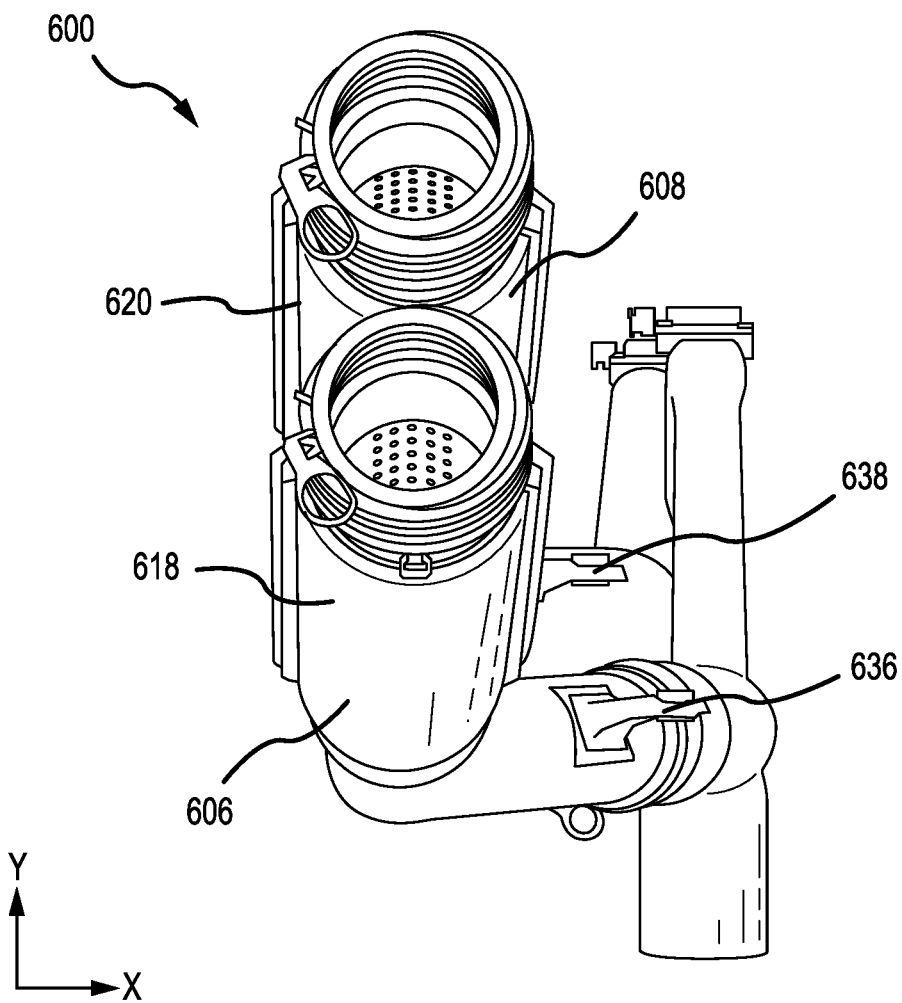
Figure 4C:
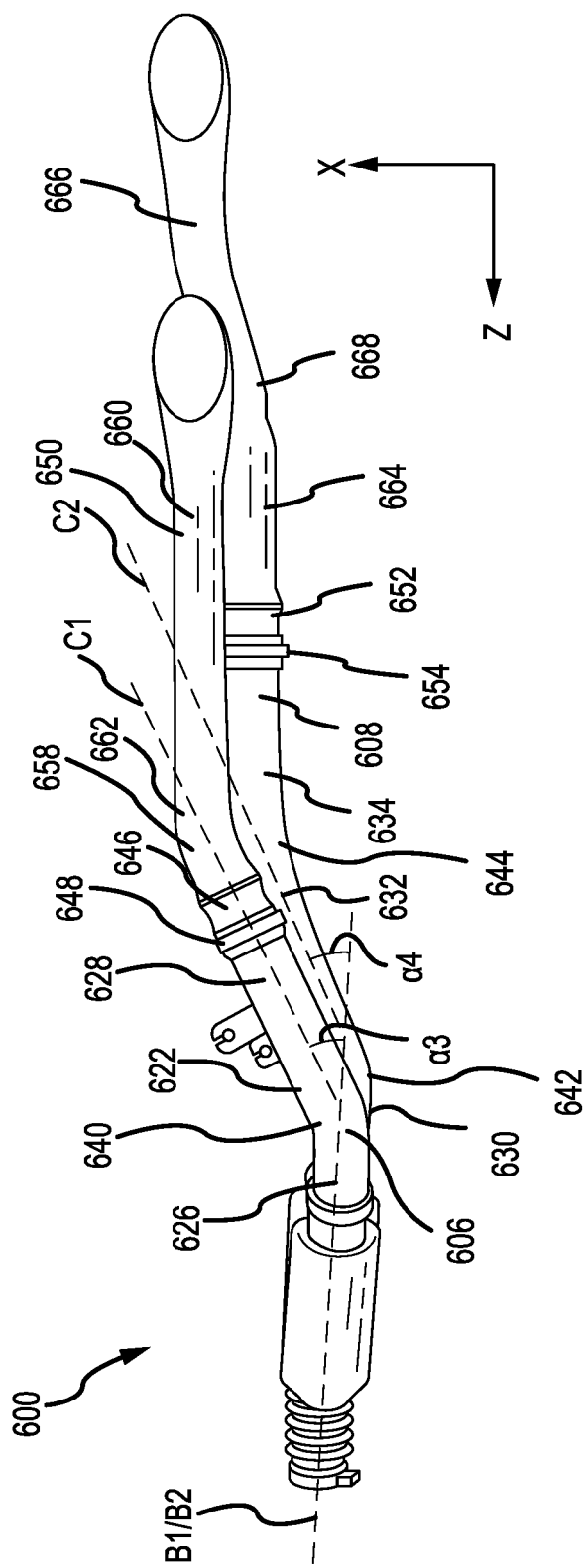
Figure 4D:
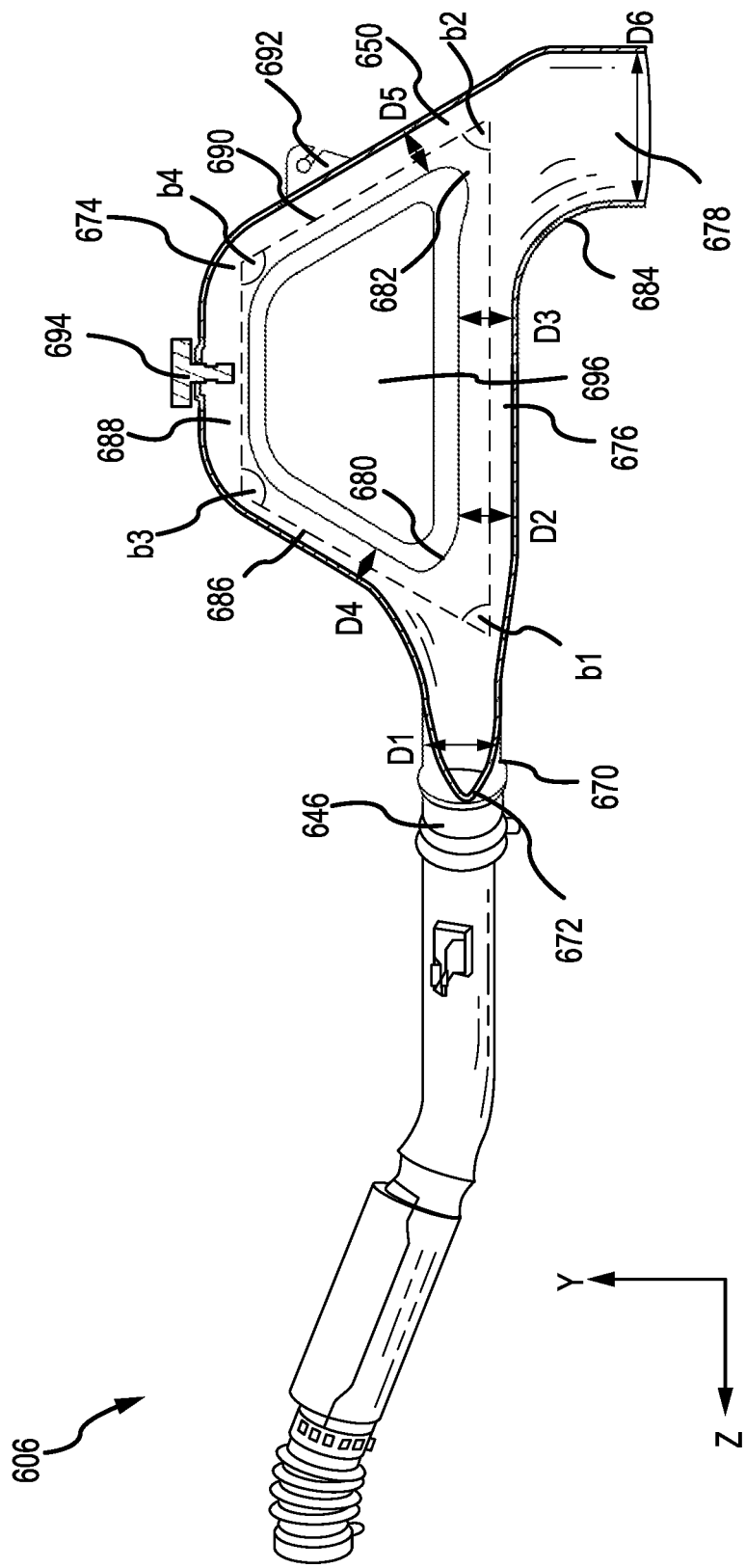

Referring now to FIGS. 4A-4C, fuel cell exhaust system 600 is illustrated from a side view, a front view, and a bottom view, respectively, in accordance with various embodiments. FIG. 4D illustrates a cross-sectional side view of first exhaust duct 606, in accordance with various embodiments. In addition to defining first exhaust pathway 602 and second exhaust pathway 604, respectively, first exhaust duct 606 and/or second exhaust duct 608 are configured to measure and monitor the amount of hydrogen in the exhaust. For example, certain regulations require that hydrogen content in FCEV exhaust be less than the lower flammability limit of hydrogen in air (for example, 4% by volume) in order to prevent the exhaust from igniting. Additionally, first exhaust duct 606 and/or second exhaust duct 608 may be structured in order to minimize pressure drop across the lengths of the exhaust ducts, maximize hydrogen mixing quality prior to measurement by one or more hydrogen sensors in first exhaust duct 606 and/or second exhaust duct 608, and to limit damage to or prevent inaccurate measurements by the one or more hydrogen sensors in first exhaust duct 606 and/or second exhaust duct 608. In various embodiments, the structures of first exhaust duct 606 and second exhaust duct 608 may lead to a hydrogen mixing quality of greater than 85%, more preferably greater than 90%, or more preferably greater than 95% at the location of the hydrogen sensors during low flow and high flow conditions. As used herein, "low flow conditions" and "high flow conditions" may refer to the velocity of the exhaust entering first exhaust duct 606 (and/or second exhaust duct 608). Low flow may be defined as an exhaust velocity of between approximately 10 to 40 meters per second (m/s) or between approximately 20 to 30 m/s. High flow may be defined as an exhaust velocity of between approximately 50 to 80 m/s or between approximately 60 to 70 m/s. In various embodiments, the structures of first exhaust duct 606 and second exhaust duct 608 may lead to a total pressure drop of less than 4 kilopascals (kPa), more preferably less than 3 kPa, or more preferably less than 2 kPa across the lengths of first exhaust duct 606 and second exhaust duct 608, respectively.

In various embodiments, first exhaust duct 606 and second exhaust duct 608 each comprise multiple components that may be manufactured separately and later coupled together; however, first exhaust duct 606 and second exhaust duct 608 are not limited in this regard and may comprise a single, integral component in various embodiments. While discussed herein as utilizing sleeve clamps, adhesives, press fittings, snap fittings, threaded connections, plastic welding, or other coupling techniques to couple two components together, it should be appreciated that the one or more components of first exhaust duct 606 and second exhaust duct 608 may be coupled in any manner capable of ensuring a fluid tight connection. Moreover, it should be appreciated that any suitable coupling method described in connection with one location could also be used in any other location.

In various embodiments, each component of first exhaust duct 606 and second exhaust duct 608 comprises an elastomeric, thermoset, or thermoplastic material such as a high-density polyethylene, polyphenylene sulfide, nitrile butadiene, acrylonitrile butadiene styrene, or polytetrafluoroethylene material. Generally, first exhaust duct 606 and second exhaust duct 608 may comprise any lightweight, chemically inert (specifically, in the presence of hydrogen) material with favorable mechanical and thermal characteristics.

In various embodiments, each component of first exhaust duct 606 and second exhaust duct 608 comprises the same or similar materials in order to ensure uniform thermal expansion and contraction, thereby decreasing the likelihood exhaust gases will leak out of first exhaust duct 606 and second exhaust duct 608 in response to temperature fluctuations. However, first exhaust duct 606 and second exhaust duct 608 are not limited in this regard and may comprise multiple components of varying materials. In various embodiments, the components of first exhaust duct 606 and second exhaust duct 608 may be formed using any suitable manufacturing technique including compression molding, injection molding, blow molding, thermoforming, additive manufacturing, or any other suitable technique.

First exhaust duct 606 comprises a first length L1 and second exhaust duct 608 comprises a second length L2. In various embodiments, first length L1 is less than second length L2; however, the lengths of first exhaust duct 606 and second exhaust duct 608 are not limited in this regard, and L1 may be equal to or greater than L2 in various embodiments. In various embodiments, first length L1 may be between approximately 1 meter and 2 meters, between approximately 1.25 meters and 1.75 meters, or approximately 1.45 meters. Second length L2 may be between approximately 1.5 meters and 2.5 meters, between 1.75 meters and 2.25 meters, or approximately 1.8 meters. When coupled to FCEV 100, a forwardmost portion of first exhaust duct 606 may be aligned in the longitudinal direction with a forwardmost portion of second exhaust duct 608, but a rearmost portion of second exhaust duct 608 may be rearward of a rearmost portion of first exhaust duct 606. First exhaust duct 606 may extend longitudinally from first exhaust outlet 514 of first fuel cell stack 502 to first exhaust aperture 122 and second exhaust duct 608 may extend longitudinally from second exhaust outlet 516 of second fuel cell stack 504 to second exhaust aperture 124.

First exhaust duct 606 comprises a first convolute duct 610 and second exhaust duct 608 comprises a second convolute duct 612. First convolute duct 610 may be positioned below second convolute duct 612 in the vertical direction but aligned with second convolute duct 612 in the transverse and longitudinal directions. In various embodiments, a first end of first convolute duct 610 is coupled to and in fluid communication with first exhaust outlet 514 of first fuel cell stack 502 and a first end of second convolute duct 612 is coupled to and in fluid communication with second exhaust outlet 516 of second fuel cell stack 504. In various embodiments, first convolute duct 610 and second convolute duct 612 each comprise a flexible or semiflexible, hollow, cylindrical tube comprising an inner diameter and an outer diameter. First convolute duct 610 may be configured to receive a pipe of first exhaust outlet 514, which may comprise a slightly smaller outer diameter than the inner diameter of first convolute duct 610. Likewise, second convolute duct 612 may be configured to receive a pipe of second exhaust outlet 516, which may comprise a slightly smaller outer diameter than the inner diameter of second convolute duct 612. However, first convolute duct 610 and second convolute duct 612 are not limited in this regard and may be configured to be inserted into, rather than receiving, the pipes of first exhaust outlet 514 and second exhaust outlet 516, respectively.

In various embodiments, first exhaust duct 606 and second exhaust duct 608 comprise a first sleeve clamp 614 and a second sleeve clamp 616, respectively. First sleeve clamp 614 and second sleeve clamp 616 may comprise a polymer or metal band extending circumferentially around the outer diameters of first convolute duct 610 and second convolute duct 612, respectively. First sleeve clamp 614 and second sleeve clamp 616 may each comprise one or more fasteners configured to be tightened, thereby reducing the diameters of first sleeve clamp 614 and second sleeve clamp 616, which may increase contact surface area and compression between first convolute duct 610 and the pipe of first exhaust outlet 514 and second convolute duct 612 and the pipe of second exhaust outlet 516. In various embodiments, first convolute duct 610 and second convolute duct 612 each include some amount flexibility in one or more dimensions. More specifically, first convolute duct 610 and second convolute duct 612 may be configured to bend in the vertical and transverse directions and expand and contract in the longitudinal direction. As a result, first convolute duct 610 and second convolute duct 612 may allow for movement of first exhaust duct 606 and second exhaust duct 608 relative to the pipes of first exhaust outlet 514 and second exhaust outlet 516, respectively, which may be caused by vibrations and/or shifting of components during vehicle operation and/or pressure fluctuations resulting from changes in flow rate into and/or out of first exhaust duct 606 and second exhaust duct 608, respectively. Moreover, the flexible nature of first convolute duct 610 and second convolute duct 612 may permit these components to be coupled to first exhaust outlet 514 and second exhaust outlet 516, respectively, without perfect alignment in the vertical and transverse directions.

First convolute duct 610 and second convolute duct 612 may be further coupled to and in fluid communication with a first resonator 618 and a second resonator 620, respectively. First resonator 618 may be positioned below second resonator 620 in the vertical direction but aligned with second resonator 620 in the transverse and longitudinal directions. In various embodiments, a second end of first convolute duct 610 is configured to receive a first end of first resonator 618 and a second end of second convolute duct 612 is configured to receive a first end of second resonator 620. In various embodiments, first exhaust duct 606 and second exhaust duct 608 may each comprise additional sleeve clamps configured to couple the convolute ducts and resonators. More specifically, in various embodiments, first exhaust duct 606 comprises a third sleeve clamp 621 and second exhaust duct 608 comprises a fourth sleeve clamp 623. Third sleeve clamp 621 and fourth sleeve clamp 623 may be similar to first sleeve clamp 614 and second sleeve clamp 616 and may be configured to increase contact surface area and compression between the convolute ducts and resonators. While illustrated and described herein as receiving the first ends of first resonator 618 and second resonator 620, respectively, first exhaust duct 606 and second exhaust duct 608 are not limited in this regard and, in various embodiments, the components may be sized such that the first ends of first resonator 618 and second resonator 620 are configured to receive the second ends of first convolute duct 610 and second convolute duct 612, respectively.

First resonator 618 and second resonator 620 are configured to reduce or eliminate noise generated as fuel cell system 500 operates and exhaust exits fuel cell exhaust system 600. For example, in various embodiments, first resonator 618 and second resonator 620 each comprise multiple concentric layers of varying diameters, separated by one or more radially extending walls, in various embodiments, first resonator 618 and second resonator 620 each comprise a first cylindrical layer having a first diameter and a second cylindrical layer having a second diameter that is concentric with the first cylindrical layer. In various embodiments, each of first resonator 618 and second resonator 620 comprise four radially extending walls (which may be orthogonal to centerlines extending through first resonator 618 and second resonator 620) coupled to and extending between the first cylindrical layer and the second cylindrical layer; however, first resonator 618 and second resonator 620 are not limited in this regard and may comprise more or fewer radially extending walls in various embodiments. The radially extending walls within first resonator 618 and second resonator 620 may define multiple chambers positioned along the lengths of the resonators. In various embodiments, first resonator 618 and second resonator 620 each comprise five chambers, each defined, in part, by the first cylindrical layer, the second cylindrical layer, and one or more of the radially extending walls. First resonator 618 and second resonator 620 may each comprise a plurality of apertures extending radially through the first cylindrical layers of first resonator 618 and second resonator 620, respectively. In various embodiments, the plurality of apertures may differ in size, shape, number, and placement across the lengths of the first resonator 618 and second resonator 620. By varying the size, shape, number, and placement of apertures between chambers, each chamber may be configured to eliminate or reduce sounds of a given frequency range.

As exhaust travels through first resonator 618 and second resonator 620, the exhaust may generate sound waves. The sound waves may travel through the plurality of apertures in the first cylindrical layers of first resonator 618 and second resonator 620, respectively, and be reflected off the inner walls of the second cylindrical layers of first resonator 618 and second resonator 620, respectively. As the reflected sound waves are returned through the plurality of apertures in the second cylindrical layers, at least some of the reflected sound waves may destructively interfere with sound waves traveling through the plurality of apertures to the second cylindrical layers. As a result, noise generated by fuel cell exhaust system 600 may be reduced.

In various embodiments, first resonator 618 and second resonator 620 are generally oriented in downward angles. For example, as illustrated in FIG. 4A, in various embodiments, first convolute duct 610 comprises a first convolute duct axis A1 extending through a centerline of first convolute duct 610 that is parallel to the longitudinal axis Z. Likewise, second convolute duct 612 comprises a second convolute duct axis A2 extending through a centerline of second convolute duct 612 that is parallel first horizontal axis A1 and longitudinal axis Z. First resonator 618 comprises a first resonator axis B1 extending through a centerline of first resonator 618. Second resonator 620 comprises a second resonator axis B2 extending through a centerline of second resonator 620. A first angle $\alpha 1$ may be defined between first convolute duct axis A1 and first resonator axis B1. Similarly, a second angle $\alpha 2$ may be defined between second convolute duct axis A2 and second resonator axis B2. In various embodiments, first angle $\alpha 1$ and second angle $\alpha 2$ may be between approximately 5° and 85°, between approximately 30° and 60°, or approximately 45°. While described herein as comprising similar angles, the orientations of first exhaust duct 606 and second exhaust duct 608 are not limited in this regard and may comprise different angles in various embodiments. The downward angles of first resonator 618 and second resonator 620 serve to increase the velocity of the exhaust traveling through first resonator 618 and second resonator 620 and also position the outlets of first resonator 618 and second resonator 620 vertically with respect to first exhaust aperture 122 and second exhaust aperture 124.

First resonator 618 is coupled to and in fluid communication with a first mid-duct 622. Similarly, second resonator 620 is coupled to and in fluid communication with a second mid-duct 624. In various embodiments, a first end of first mid-duct 622 comprises a diameter substantially equal to that of a second end of first resonator 618. Similarly, a first end of second mid-duct 624 comprises a diameter substantially equal to that of a second end of second resonator 620. The second end of first resonator 618 and the first end of first mid-duct 622 may be coaxially aligned and coupled together utilizing an adhesive, plastic welding, press fitting, or other suitable technique to couple the components together in a fluid tight manner. Similarly, the second end of second resonator 620 and the first end of second mid-duct 624 may be coaxially aligned and coupled together in a similar manner.

First mid-duct 622 comprises a first segment 626 and a second segment 628. Second mid-duct 624 comprises a first segment 630, a second segment 632, and a third segment 634. First mid-duct 622 further comprises a first mounting bracket 636 coupled to second segment 628 and second mid-duct 624 further comprises a second mounting bracket 638 coupled to second segment 632. First mounting bracket 636 and second mounting bracket 638 may be configured to receive one or more fasteners configured to couple first exhaust duct 606 and second exhaust duct 608, respectively, to FCEV 100. In various embodiments, first exhaust duct 606 and second exhaust duct 608 may be coupled directly or indirectly (via first mounting bracket 636 and second mounting bracket 638, respectively) to at least one frame rail of chassis 104, a battery frame assembly, and/or a hydrogen storage frame.

In various embodiments, first segment 626 of first mid-duct 622 is coaxially aligned with first resonator 618. Stated otherwise, first resonator axis B1 may extend through first resonator 618 and through a centerline of first segment 626. Similarly, first segment 630 of second mid-duct 624 is coaxially aligned with second resonator 620. Stated otherwise, second resonator axis B2 may extend through second resonator 620 and through a centerline of first segment 630. In various embodiments, first segment 626 of first mid-duct 622 comprises a length less than that of first segment 630 of second mid-duct 624.

In various embodiments, second segment 628 of first-mid duct 622 is angled relative to first segment 626 of first mid-duct 622. Similarly, second segment 632 of second mid-duct 624 is angled relative to first segment 630 of second mid-duct 624. Second segment 628 and second segment 632 may be angled for packaging purposes, for example. More specifically, when coupled to FCEV 100, first convolute duct 610, first resonator 618, and first segment 626 of first exhaust duct 606 may be positioned longitudinally forward but transversely aligned with a high voltage battery pack positioned between the frame rails of chassis 104. Similarly, second convolute duct 612, second resonator 620, and first segment 630 of second exhaust duct 608 may be positioned longitudinally forward but transversely aligned with the high voltage battery pack. By angling second segment 628 of first-mid duct 622 and second segment 632 of second mid-duct 624, first exhaust duct 606 and second exhaust duct 608 may overlap with the battery pack in the longitudinal direction without the need to reposition the battery pack or extend the length or otherwise alter the structure of first exhaust duct 606 or second exhaust duct 608. In various embodiments, second segment 628 and second segment 632 may be angled such that outlets of first exhaust duct 606 and second exhaust duct 608 align transversely with first fuel cell exhaust aperture 122 and second fuel cell exhaust aperture 124, respectively, which may be located transversely between the battery pack and at least one frame rail of chassis 104.

With reference to FIG. 4C, first exhaust duct 606 and second exhaust duct 608 are illustrated from a bottom view. First exhaust duct 606 comprises a first segment axis C1 and second exhaust duct 608 comprises a second segment axis C2. In various embodiments, first segment axis C1 forms a third angle $\alpha 3$ with first resonator axis B1 (or second resonator axis B2) and second segment axis C2 forms a fourth angle $\alpha 4$ with first resonator axis B1 (or second resonator axis B2). In various embodiments, third angle $\alpha 3$ may be between approximately 0° and 30°, between approximately 10° and 20°, or approximately 15°. Fourth angle $\alpha 4$ may be between approximately 0° and 40°, between approximately 10° and 30°, or approximately 20°. In various embodiments, third angle $\alpha 3$ may be greater than fourth angle $\alpha 4$; however, fuel cell exhaust system 600 is not limited in this regard and third angle $\alpha 3$ may be equal to or less than fourth angle $\alpha 4$ in various embodiments.

In various embodiments, second segment 628 of first mid-duct 622 terminates at a second end of first mid-duct 622, which may be coaxially aligned with first segment axis C1. When viewed from the bottom (perpendicular to the Z-X plane), first mid-duct 622 comprises a first bend 640 through which first segment 626 transitions into second segment 628. In contrast, second segment 632 of second mid-duct 624 transitions to third segment 634 which may be substantially parallel and offset in the transverse direction from first segment 630 of second mid-duct 624. When viewed from the bottom (perpendicular to the Z-X plane), second mid-duct 624 comprises a second bend 642 through which first segment 630 transitions into second segment 632 and a third bend 644 through which second segment 632 transitions into third segment 634. In various embodiments, first bend 640 and second bend 642 may be bent in the same direction but third bend 644 may be bent in the opposite direction as first bend 640 and second bend 642. The various segments and bends discussed above may not only assist in efficient packaging in FCEV 100 but may also contribute to increasing mixing quality of the exhaust by periodically redirecting the exhaust flow path.

The second end of first mid-duct 622 is coupled to and in fluid communication with a first coupling duct 646. In various embodiments, first coupling duct 646 may be coaxially aligned with second segment axis C2 and second segment 628 of first mid-duct 622. A first end of first coupling duct 646 may be configured to receive the second end of first mid-duct 622. For example, in various embodiments, the second end of first mid-duct 622 may comprise an outer diameter slightly smaller than an inner diameter of the first end of first coupling duct 646. After being inserted into the first end of first coupling duct 646, a fifth sleeve clamp 648 may be tightened around the outer diameter of the first end of first coupling duct 646, thereby compressing the first end of first coupling duct 646 around the second end of first mid-duct 622. A second end of first coupling duct 646 may be coupled to and in fluid communication with a first end of a first tail duct 650 utilizing any suitable technique, including using sleeve clamps, adhesives, press fittings, snap fittings, threaded connections, plastic welding, or other technique.

Similarly, a second end of second mid-duct 624 is coupled to and in fluid communication with a second coupling duct 652. In various embodiments, second coupling duct 652 may be coaxially aligned with third segment 634 of second mid-duct 624. A first end of second coupling duct 652 may be configured to receive the second end of second mid-duct 624. For example, in various embodiments, the second end of second mid-duct 624 may comprise an outer diameter slightly smaller than an inner diameter of the first end of second coupling duct 652. After being inserted into the first end of second coupling duct 652, a sixth sleeve clamp 654 may be tightened around the outer diameter of the first end of second coupling duct 652, thereby compressing the first end of second coupling duct 652 around the second end of second mid-duct 624. A second end of second coupling duct 652 may be coupled to and in fluid communication with a first end of a second tail duct 656 utilizing any suitable technique, including using sleeve clamps, adhesives, press fittings, snap fittings, threaded connections, plastic welding, or other technique.

In various embodiments, first tail duct 650 and second tail duct 656 each comprise multiple segments that may define additional bends. For example, in various embodiments, first tail duct 650 comprises a first segment 658 and a second segment 660. First segment 658 may be coaxially aligned with first coupling duct 646 and second segment 628 of first mid-duct 622. In various embodiments, first segment 658 may transition into second segment 660 via a fourth bend 662. Similar to the other bends discussed above, fourth bend 662 may assist in efficient packaging of first exhaust duct 606 and also increase mixing quality of the exhaust gases.

Similarly, second tail duct 656 comprises a first segment 664 and a second segment 666. First segment 664 may be coaxially aligned with second coupling duct 652 and third segment 634 of second mid-duct 624. In various embodiments, first segment 664 may transition into second segment 666 via a fifth bend 668. Similar to the other bends discussed above, fifth bend 668 may assist in efficient packaging of second exhaust duct 608 and also increase hydrogen mixing quality within the exhaust. Fifth bend 668 may be oriented in the opposite direction as fourth bend 662 of first tail duct 650. For example, in various embodiments, third segment 634 of second mid-duct 624, second coupling duct 652, and first segment 664 of second tail duct 656 may be offset from second segment 660 of first tail duct 650 (in the negative X-direction). Fifth bend 668 may be bent (in the positive X-direction) such that an outlet of second tail duct 656 aligns with an outlet of first tail duct 650 in the transverse direction when coupled to FCEV 100.

With reference to FIG. 4D, a cross-sectional view of first tail duct 650 is illustrated, in accordance with various embodiments. In various embodiments, the structure of second tail duct 656 of second exhaust duct 608 may be identical to or substantially similar to the structure of first tail duct 650 (aside from differences in the locations and directions of bends), so the structure of second tail duct 656 will not be discussed in detail herein for sake of brevity. In general, first tail duct 650 (and second tail duct 656) may be configured to receive exhaust from first coupling duct 646 (and other upstream components of first exhaust duct 606), route at least a portion of the exhaust to a hydrogen sensor in order to measure the amount of hydrogen present in the exhaust, and deliver the exhaust to the external environment.

In various embodiments, first tail duct 650 comprises an inlet duct 670 that is in fluid communication with an outlet 672 of first coupling duct 646. Inlet duct 670 may be in fluid communication with an upper duct 674 and a lower duct 676, each of which may be configured to receive at least a portion of the exhaust from inlet duct 670. In various embodiments, upper duct 674 and lower duct 676 may also be in fluid communication with an outlet duct 678, which may be configured to receive exhaust from upper duct 674 and lower duct 676 and deliver the exhaust to the external environment. Inlet duct 670 may diverge into upper duct 674 and lower duct 676 at a first fork 680. Upper duct 674 and lower duct 676 may converge at a second fork 682 into outlet duct 678. In various embodiments, first tail duct 650 comprises a trapezoidal shaped cutout 696 between upper duct 674 and lower duct 676, which may reduce the weight of first tail duct 650 (and first exhaust duct 606).

In various embodiments, lower duct 676 is substantially aligned with inlet duct 670 in the vertical direction. In various embodiments, lower duct 676 may be slightly lower or slightly higher in the vertical direction that inlet duct 670. For example, as illustrated in FIG. 4D, a centerline of lower duct 676 is slightly lower in the vertical direction than a centerline of inlet duct 670; however, lower duct 676 is not limited in this regard and the centerline of lower duct 676 may be coaxially aligned with or positioned vertically above the centerline of inlet duct 670 in various embodiments. In various embodiments, lower duct 676 may transition into outlet duct 678 via a sixth bend 684.

Upper duct 674 comprises an incline duct 686, a transition duct 688, and a decline duct 690. In various embodiments, incline duct 686, transition duct 688, and decline duct 690 are in fluid communication such that at least a portion of the exhaust may flow from inlet duct 670 through incline duct 686, through transition duct 688, and through decline duct 690 into outlet duct 678. In various embodiments, inlet duct 670 transitions into incline duct 686 via a seventh bend, incline duct 686 transitions into transition duct 688 via an eighth bend, transition duct 688 transitions into decline duct 690 via a ninth bend, and decline duct 690 transitions into outlet duct 678 via a tenth bend. Each bend described above may further increase the hydrogen mixing quality in the exhaust. First tail duct 650 may further comprise a mounting bracket 692 coupled to incline duct 686 that may be configured to directly or indirectly secure first exhaust duct 606 (and first tail duct 650) to at least one frame rail of chassis 104. In various embodiments, mounting bracket 692 may be configured to receive a fastener that may also extend through a mounting bracket on a second tail duct 656 of second exhaust duct 608. As a result, a single fastener may be configured to couple both first exhaust duct 606 and second exhaust duct 608 to chassis 104.

In various embodiments, first tail duct 650 comprises a hydrogen sensor 694 that may be coupled to and extend through first tail duct 650. Hydrogen sensor 694 may be configured to measure hydrogen content in the exhaust. For example, excessively high amounts of hydrogen in the exhaust may indicate an issue with the operation or performance of fuel cell system 500, and therefore may be beneficial to measure and monitor. In various embodiments, hydrogen sensor 694 may be configured to measure the hydrogen content in the exhaust and send a signal to one or more control units and/or infotainment displays via one or more controller area network (CAN) signals, which may indicate fuel cell system 500 needs to be shut down and/or alert an operator of FCEV 100 in the event a measured hydrogen content in the exhaust exceed a threshold value (for example, 4% by volume). Hydrogen sensor 694 may comprise any suitable hydrogen sensor including an electrochemical sensor, microelectromechanical (MEMS) sensor, thin film sensor, thick film sensor, chemochromic sensor, diode-based sensor, or other sensor type.

Hydrogen sensor 694 may be located on and/or in first tail duct 650 such that hydrogen sensor 694 encounters a sufficiently homogenous or representative sample of the exhaust, while also minimizing the amount of moisture hydrogen sensor 694 encounters. For example, for hydrogen sensor 694 to provide reliable and useful data, the amount of hydrogen measured by hydrogen sensor 694 must correlate with the amount of hydrogen present in the exhaust exiting fuel cell system 500. Excess moisture in and around hydrogen sensor 694 may damage hydrogen sensor 694 and/or adversely affect hydrogen sensor 694's ability to accurately measure hydrogen content in the exhaust. Due to the relative densities of hydrogen (approximately 0.089 kg/m$^3$ at 20° C.), air (approximately 1.205 kg/m$^3$ at 20° C.), and water vapor (approximately 0.804 kg/m$^3$ at 20° C.), exhaust constituents may tend to accumulate in different portions of first exhaust duct 606 and second exhaust duct 608. For example, because water (and water vapor) has a higher density than air and hydrogen, water (and/or water vapor) may tend to accumulate in the lower portions of first exhaust duct 606 due to gravity. Likewise, hydrogen, which has the lowest density amongst the exhaust gas constituents, may tend to accumulate in the upper portions of first exhaust duct 606. As such, in various embodiments, hydrogen sensor 694 is coupled to a top surface of transition duct 688, which may be elevated relative to the remaining portions and components of first exhaust duct 606. More specifically, in various embodiments, hydrogen sensor 694 is located vertically above and extends through transition duct 688 at or near a longitudinal midpoint of transition duct 688. However, hydrogen sensor 694 is not limited in this regard and may be coupled to other suitable portions of first tail duct 650, including at any longitudinal point on incline duct 686, transition duct 688, or decline duct 690. As a result, hydrogen sensor 694 may be positioned above areas of water (and/or water vapor) accumulation in first exhaust duct 606. The structure and position of hydrogen sensor 694 is discussed in additional detail below in relation to FIGS. 5A-5C.

In addition to minimizing the amount of moisture hydrogen sensor 694 encounters as a result of water present in the exhaust, the structure of first exhaust duct 606 (and first tail duct 650) may also isolate hydrogen sensor 694 from water external to FCEV 100. For example, when operating in wet conditions as a result of rain, snow, flooding, etc.), FCEV 100 may traverse water that is sufficiently deep (for example, up to 0.5 meters) to cause water to flow into outlet duct 678 and into other portions of first exhaust duct 606, including lower duct 676. As such, hydrogen sensor 694 may be located a sufficient distance above a ground surface and lower duct 676 such that water cannot reach hydrogen sensor 694. In various embodiments, hydrogen sensor 694 is located between approximately 0.1 meters and 0.3 meters, between approximately 0.15 meters and 0.25 meters, or approximately 0.235 meters above lower duct 676 and located between 0.6 meters and 0.8 meters, between approximately 0.65 meters and 0.75 meters, or approximately 0.735 meters above the ground surface.

In various embodiments, incline duct 686 and decline duct 690 may be situated at an angle relative to lower duct 676 and transition duct 688. For example, in various embodiments, a first angle $\beta 1$ may be defined between the centerline of lower duct 676 and a centerline of incline duct 686. In various embodiments, first angle fit $\beta 1$ may be between approximately 5° and 85°, between approximately 25° and 65°, or approximately 45°. A second angle $\beta 2$ may be defined between the centerline of lower duct 676 and a centerline of decline duct 690. In various embodiments, second angle may be between approximately 5° and 85°, between approximately 25° and 65°, or approximately 45°. While described herein as comprising similar angles, first angle $\beta 1$ and second angle $\beta 2$ are not limited in this regard and may comprise different angles in various embodiments. A third angle $\beta 3$ may be defined between the centerline of incline duct 686 and a centerline of transition duct 688. In various embodiments, third angle $\beta 3$ may be between approximately 5" and 85°, between approximately 25° and 65°, or approximately 45°. A fourth angle $\beta 4$ may be defined between the centerline of decline duct 690 and the centerline of transition duct 688. In various embodiments, fourth angle $\beta 4$ may be between approximately 5° and 85°, between approximately 25° and 65°, or approximately 45°. While described herein as comprising similar angles, third angle $\beta 3$ and fourth angle $\beta 4$ are not limited in this regard and may comprise different angles in various embodiments.

Inlet duct 670 comprises a first diameter D1 at a location adjacent to first coupling duct 646. Lower duct 676 comprises a second diameter D2 and a third diameter D3. In various embodiments, second diameter D2 may be located downstream and adjacent to first fork 680 and third diameter D3 may be located upstream and adjacent to second fork 682. Upper duct 674 comprises a fourth diameter D4 and a fifth diameter D5. In various embodiments, fourth diameter D4 may be located downstream and adjacent to first fork 680 and fifth diameter D5 may be located upstream and adjacent to second fork 682. Outlet duct 678 comprises a sixth diameter D6. In various embodiments, sixth diameter D6 may be located downstream and adjacent to second fork 682.

In various embodiments, first diameter D1 is greater than second diameter D2 and third diameter D3. For example, first diameter D1 may be between approximately 0.04 meters and 0.08 meters, between approximately 0.05 meters and 0.07 meters, or approximately 0.064 meters. Second diameter D2 may be between approximately 0.03 meters and 0.07 meters, between approximately 0.04 meters and 0.06 meters, or approximately 0.056 meters. Third diameter D3 may be between approximately 0.03 meters and 0.07 meters, between approximately 0.04 meters and 0.06 meters, or approximately 0.056 meters. Second diameter D2 and third diameter D3 are greater than fourth diameter D4, which is greater than fifth diameter D5. In various embodiments, fourth diameter D4 may be between approximately 0.02 meters and 0.06 meters, between approximately 0.03 meters and 0.05 meters, or approximately 0.045 meters. Fifth diameter D5 may be between approximately 0.02 meters and 0.06 meters, between approximately 0.03 meters and 0.05 meters, or approximately 0.045 meters. Sixth diameter D6 is greater than the first diameter through the fifth diameter. In various embodiments, sixth diameter D6 is between approximately 0.001 meters and 0.015 meters, between approximately 0.05 meters and 0.2 meters, between approximately 0.1 meters and 0.15 meters, or approximately 0.136 meters.

The structure of first tail duct 650 (and similarly, second tail duct 656) ensures an adequate and sufficiently representative supply of exhaust is delivered to hydrogen sensor 694 while also minimizing pressure losses and limiting hydrogen sensor 694's exposure to moisture. For example, second diameter D2 and third diameter D3 of lower duct 676 and fourth diameter D4 of upper duct 674 may be sized such that a majority of the exhaust travels through lower duct 676 rather than upper duct 674 (to maintain an adequate flow rate and velocity) but a sufficient amount of the exhaust travels through upper duct 674 in order to be measured by hydrogen sensor 694. Moreover, first angle β1 may be large enough to position hydrogen sensor 694 a sufficient vertical distance from areas most likely to accumulate moisture in first exhaust duct 606 but small enough in order to avoid excessive pressure and velocity losses.

As discussed herein, the structures of first exhaust duct 606 and second exhaust duct 608 may be configured to: reduce and/or minimize pressure drop across the lengths of first exhaust duct 606 and second exhaust duct 608, respectively; increase and/or maximize hydrogen mixing quality in the exhaust upstream of and/or at the location of the hydrogen sensor(s); ensure the exhaust maintains a sufficient velocity to exit first exhaust duct 606 and second exhaust duct 608 at low flow and high flow conditions; limit the amount of moisture (water and/or water vapor) the hydrogen sensor(s) are exposed to; and allow for efficient packaging of fuel cell exhaust system 600 on FCEV 100. Moreover, the structures of first exhaust duct 606 and second exhaust duct 608 may allow for easy assembly and component replacement while also being durable in response to shock and vibration forces.

As can be seen from Table 1 below, in an exemplary embodiment, first exhaust duct 606 and second exhaust duct 608 each generate a total pressure loss of less than 2 kPa. As used herein, total pressure loss is defined as the sum of static pressure losses and dynamic pressure losses of each major component included in first exhaust duct 606 and second exhaust duct 608. First exhaust duct 606 generates a total pressure loss of approximately 1.84 kPa and second exhaust duct 608 generates a total pressure loss of approximately 1.88 kPa. Due to their relatively large diameters, first fork 680, second fork 682, and outlet duct 678 may each assist in reducing pressure losses, which may partially compensate for pressure losses resulting from the various bends in first exhaust duct 606 and second exhaust duct 608.

TABLE 1

| Total Pressure Loss | |
| --- | --- |
| Location | Total Pressure Loss (kPa) |
| First Convolute Duct | 0.17 |
| First Resonator | 0.43 |
| First Mid-duct | 0.34 |
| First Tail Duct | 0.90 |
| First Exhaust Duct Total | 1.84 |
| Second Convolute Duct | 0.22 |
| Second Resonator | 0.42 |
| Second Mid-duct | 0.46 |
| Second Tail Duct | 0.78 |
| Second Exhaust Duct Total | 1.88 |

Moreover, as can be seen from Table 2 and Table 3 below, first exhaust duct 606 and second exhaust duct 608 each result in a hydrogen mixing quality of at least 95% at the locations of their respective hydrogen sensors. For example, in an exemplary embodiment, in high flow conditions, first tail duct 650 may lead to a hydrogen mixing quality ranging from approximately 98.2% at first inlet duct 670 to approximately 99.6% at the location of hydrogen sensor 694. Second tail duct 656 may lead to a hydrogen mixing quality ranging from approximately 96.7% at a second inlet duct to approximately 99.8% at a location of a second hydrogen sensor. In low flow conditions, first tail duct 650 may lead to a hydrogen mixing quality ranging from approximately 94.9% at first inlet duct 670 to approximately 99.5% at the location of hydrogen sensor 694. Second tail duct 656 may lead to a hydrogen mixing quality ranging from approximately 96.0% at the second inlet duct to approximately 99.9% at the location of the second hydrogen sensor. As a result, the accuracy of hydrogen measurements in fuel cell exhaust system 600 may be increased.

TABLE 2

| Tail Duct Mixing Quality at High Flow Conditions | | | |
| --- | --- | --- | --- |
| Location | $H_2$ Mixing Quality | $H_2$ Volume Fraction | Average Velocity (m/s) |
| First Inlet Duct | 98.2 | 8.00 | — |
| First Lower Duct | 99.1 | 7.99 | — |
| First Hydrogen Sensor | 99.6 | 7.88 | 39.65 |
| Second Inlet Duct | 96.7 | 8.00 | — |
| Second Lower Duct | 98.6 | 7.87 | — |
| Second Hydrogen Sensor | 99.8 | 8.43 | 39.83 |

TABLE 3

| Tail Duct Mixing Quality at Low Flow Conditions | | | |
| --- | --- | --- | --- |
| Location | $H_2$ Mixing Quality | $H_2$ Volume Fraction | Average Velocity (m/s) |
| First Inlet Duct | 94.9 | 7.99 | — |
| First Lower Duct | 97.1 | 7.87 | — |
| First Hydrogen Sensor | 99.5 | 8.35 | 9.56 |

TABLE 3-continued

Tail Duct Mixing Quality at Low Flow Conditions

| Location | $H_2$ Mixing Quality | $H_2$ Volume Fraction | Average Velocity (m/s) |
|---|---|---|---|
| Second Inlet Duct | 96.0 | 7.99 | — |
| Second Lower Duct | 98.7 | 7.80 | — |
| Second Hydrogen Sensor | 99.9 | 8.86 | 5.61 |

Figure 5C:
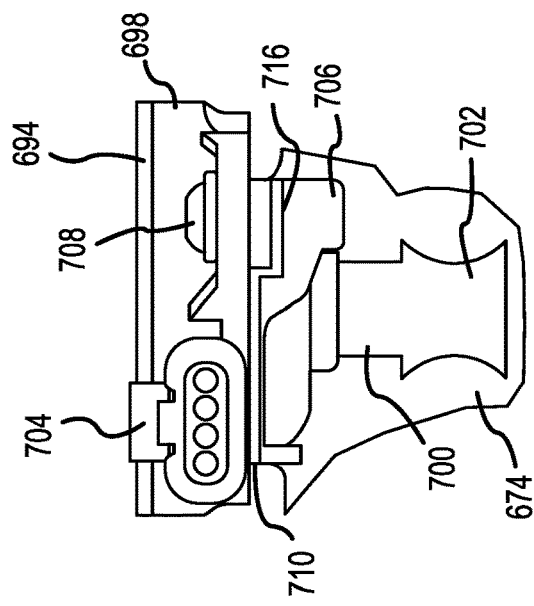
FIGS. 5A-5C illustrate detailed views of a hydrogen sensor of a fuel cell exhaust system, in accordance with various embodiments.
Figure 5B:
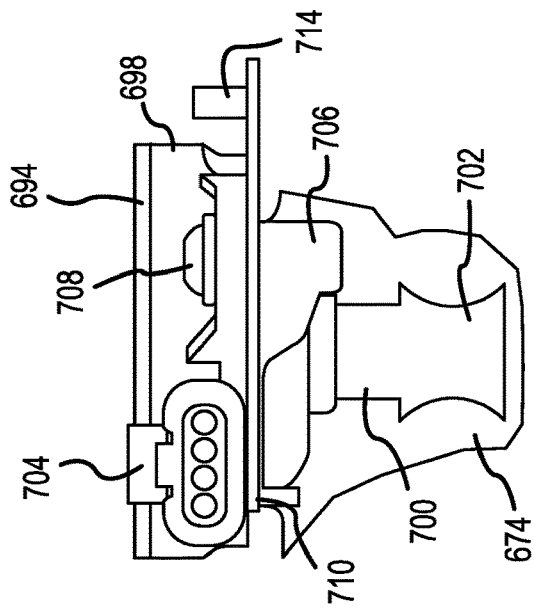
Figure 5A:
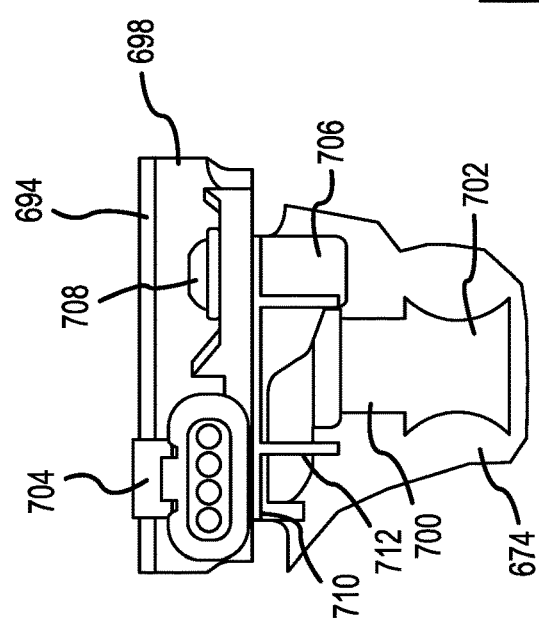

Referring now to FIGS. 5A-5C, various detailed views of hydrogen sensor 694 coupled to upper duct 674 are illustrated, in accordance with various embodiments. In various embodiments, hydrogen sensor 694 comprises a body 698, a neck 700, and a sensor element 702. Body 698, which may be external to upper duct 674, may comprise a communications connector 704 to enable collected and/or processed data to be communicated to other FCEV 100 control units or processors. Neck 700 may be configured to be inserted into upper duct 674 (for example, via an aperture formed through the exterior surface of upper duct 674) in order to allow sensor element 702 to be positioned such that sensor element 702 is exposed to the fuel cell exhaust. In various embodiments, hydrogen sensor 694 is coupled to upper duct 674 via an adapter 706 using a first fastener 708; however, in other embodiments, hydrogen sensor 694 is coupled directly to upper duct 674 without use of adapter 706.

In various embodiments, first exhaust duct 606 and second exhaust duct 608 are equipped with one or more features configured to minimize and/or discharge static electricity generated as a result of the exhaust flowing through the exhaust ducts. More specifically, during high flow conditions, air and water vapor flowing through first exhaust duct 606 and second exhaust duct 608 may generate static electricity due to frictional forces between the exhaust and inner walls of the exhaust ducts. In certain circumstances (for example, when the electric potential associated with the built-up static electricity exceeds about 10 kV), the static electricity may adversely impact or prevent the ability of hydrogen sensor 694 to accurately measure the hydrogen content in the exhaust. To prevent this, first exhaust duct 606 and second exhaust duct 608 may be grounded at one or more points, for example to chassis 104.

More specifically, in various embodiments, hydrogen sensor 694 comprises a shim 710 positioned at least partially between body 698 and adapter 706 (or upper duct 674). In various embodiments, shim 710 comprises a substantially planar, electrically conductive material or materials, for example, copper, aluminum, silver, zinc, or alloys or combinations of the same. In some exemplary embodiments, shim 710 comprises a copper tape or foil. As illustrated in FIG. 5A, shim 710 comprises one or more vertically extending members 712 partially surrounding neck 700. In some embodiments, vertically extending members 712 comprise a first member upstream of neck 700 and a second member downstream of neck 700. In other embodiments, vertically extending members 712 comprise a substantially cylindrical-shaped structure that surrounds neck 700. Static electricity generated by the exhaust is attracted to shim 710 due to its conductive properties. In various embodiments, static electricity may be discharged by connecting a ground wire (not illustrated) to first fastener 708 and chassis 104, for example. In other embodiments, and as illustrated in FIG. 5B, shim 710 extends away from hydrogen sensor 694 and comprises a second fastener 714 for grounding. In other embodiments, shim 710 comprises one or more steps 716 to allow a ground wire to be coupled to first fastener 708 between adapter 706 and body 698.

While discussed above in relation to FIGS. 5A-5C as utilizing a shim 710, it should be appreciated that first exhaust duct 606, second exhaust duct 608, and hydrogen sensor 794 are not limited in this regard, and static electricity may be disposed of in other suitable ways. More specifically, in various embodiments, first exhaust duct 606 and/or second exhaust duct 608 may be formed using a resin with anti-static properties, for example, an epoxy, polyurethane, polyamide, polypropylene oxide, polyetherimide, or other resin having an increased carbon content. In other embodiments, one or more components of first exhaust duct 606 and/or second exhaust duct 608 may be coated with an electrically conductive paint, for example, a copper- or nickel-containing paint, and grounded to chassis 104. In other embodiments, one or more components of first exhaust duct 606 and/or second exhaust duct 608 comprise an overmolded metallic mesh wrap or wire liner that may be grounded to chassis 104. In still other embodiments, first exhaust duct 606 and/or second exhaust duct 608 comprise one or more conductive mesh inserts which may correspond substantially to the cross-sectional shape of the respective exhaust ducts. The conductive mesh inserts may be positioned internal to the exhaust duct and substantially perpendicular to the direction of exhaust flow. The conductive mesh inserts may be grounded to chassis 104. Moreover, in other embodiments, one or more holes or slats may be formed in one or more components of first exhaust duct 606 and/or second exhaust duct 608. The one or more holes or slots may be covered, wrapped, or filled with a conductive material and grounded to chassis 104. Numerous embodiments for minimizing and/or discharging static electricity are contemplated in this regard. Additionally, in some embodiments, components or techniques utilized for minimizing and/or discharging static electricity buildup on first exhaust duct 606 may be the same as those utilized on second exhaust duct 608. In other embodiments, the components or techniques utilized for first exhaust duct 606 differ from those utilized on second exhaust duct 608.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching may be used throughout the figures to denote different parts but not necessarily to denote the same or different materials.

Methods, systems, and articles are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements hut may include other elements not expressly listed or inherent to such process, method, article, or apparatus.

What is claimed is:

1. A fuel cell exhaust system for a fuel cell electric vehicle (FCEV), comprising:
    a first exhaust duct comprising a first tail duct, the first tail duct comprising a first lower duct and a first upper duct positioned vertically above the first lower duct;
    a second exhaust duct comprising a second tail duct, the second tail duct comprising a second lower duct and a second upper duct positioned vertically above the second lower duct;
    a first hydrogen sensor having a portion positioned within the first upper duct; and
    a second hydrogen sensor having a portion positioned within the second upper duct,
    wherein a first portion of a first exhaust is diverted to the first upper duct and measured by the first hydrogen sensor to determine hydrogen content of the first exhaust, and
    wherein a first portion of a second exhaust is diverted to the second upper duct and measured by the second hydrogen sensor to determine hydrogen content of the second exhaust.

2. The fuel cell exhaust system of claim 1, wherein the first exhaust duct is coupled to and in fluid communication with a first exhaust outlet of a first fuel cell stack and the second exhaust duct is coupled to and in fluid communication with a second exhaust outlet of a second fuel cell stack.

3. The fuel cell exhaust system of claim 2, wherein the first exhaust duct comprises a first convolute duct coupled to and in fluid communication with the first exhaust outlet of the first fuel cell stack.

4. The fuel cell exhaust system of claim 2, wherein the second exhaust duct comprises a second convolute duct coupled to and in fluid communication with the second exhaust outlet of the second fuel cell stack.

5. The fuel cell exhaust system of claim 3, wherein the first exhaust duct further comprises a first resonator coupled to and in fluid communication with the first convolute duct and a first mid-duct coupled to and in fluid communication with the first resonator.

6. The fuel cell exhaust system of claim 4, wherein the second exhaust duct further comprises a second resonator coupled to and in fluid communication with the second convolute duct and a second mid-duct coupled to and in fluid communication with the second resonator.

7. The fuel cell exhaust system of claim 5, wherein the first resonator is angled downward relative to at least a portion of the first convolute duct.

8. The fuel cell exhaust system of claim 6, wherein the second resonator is angled downward relative to at least a portion of the second convolute duct.

9. The fuel cell exhaust system of claim 1, wherein the first hydrogen sensor comprises a shim configured to discharge static electricity.

10. An exhaust duct of a fuel cell exhaust system, comprising:
    a convolute duct;
    a resonator coupled to and in fluid communication with the convolute duct;
    a mid-duct coupled to and in fluid communication with the resonator; and
    a tail duet coupled to and in fluid communication with the mid-duct, the tail duct comprising a lower duct and an upper duct,
    wherein the upper duct comprises an incline duct, a transition duct, a decline duct, and a hydrogen sensor having a portion positioned within the transition duct, and
    wherein a first portion of an exhaust is diverted to the lower duct and a second portion of the exhaust is diverted to the upper duct and measured by the hydrogen sensor to determine hydrogen content of the exhaust.

11. The exhaust duct of claim 10, wherein the tail duct further comprises an inlet duct in fluid communication with the upper duct and the lower duct and an outlet duct in fluid communication with the upper duct and the lower duct.

12. The exhaust duct of claim 11, wherein the inlet duct diverges into the upper duct and the lower duct at a first fork.

13. The exhaust duct of claim 12, wherein the upper duct and the lower duct converge into the outlet duct at a second fork.

14. The exhaust duct of claim 10, wherein the mid-duct comprises at least two segments separated by at least one bend.

15. The exhaust duct of claim 10, further comprising a first angle between the lower duct and the incline duct, a second angle between the lower duct and the decline duct, a third angle between the incline duct and the transition duct, and a fourth angle between the transition duct and the decline duct.

16. The exhaust duct of claim 10, further comprising a trapezoidal cutout between the upper duct and the lower duct.

17. The exhaust duct of claim 10, further comprising a mounting bracket coupled to the mid-duct configured to couple the exhaust duct directly or indirectly to a chassis of a fuel cell electric vehicle (FCEV).

18. A fuel gas management system of a fuel cell electric vehicle (FCEV), comprising:
    an air intake system coupled to and in fluid communication with a fuel cell system;
    a hydrogen storage system coupled to and in fluid communication with the fuel cell system; and a fuel cell exhaust system coupled to and in fluid communication with the fuel cell system, the fuel cell exhaust system comprising:
- a first exhaust duct comprising a first lower duct and a first upper duct positioned vertically above the first lower duct; and
- a first hydrogen sensor having a portion positioned within the first upper duct, wherein a portion of an exhaust is diverted to the first upper duct and measured by the first hydrogen sensor to determine hydrogen content of the exhaust.

19. The fuel gas management system of claim 18, further comprising a second exhaust duct comprising a second lower duct and a second upper duct positioned vertically above the second lower duct.

20. The fuel gas management system of claim 19, wherein the first exhaust duct is coupled to and in fluid communication with a first exhaust outlet of a first fuel cell stack of the fuel cell system and the second exhaust duct is coupled to and in fluid communication with a second exhaust outlet of a second fuel cell stack of the fuel cell system.

\* \* \* \* \*